(12) United States Patent
Meridew

(10) Patent No.: US 8,556,985 B2
(45) Date of Patent: Oct. 15, 2013

(54) ACETABULAR CUP FIXATION

(75) Inventor: Jason D. Meridew, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/299,663

(22) Filed: Nov. 18, 2011

(65) Prior Publication Data

US 2012/0065736 A1   Mar. 15, 2012

Related U.S. Application Data

(62) Division of application No. 12/370,951, filed on Feb. 13, 2009, now abandoned.

(60) Provisional application No. 61/030,027, filed on Feb. 20, 2008.

(51) Int. Cl.
*A61F 2/32* (2006.01)

(52) U.S. Cl.
USPC ..................... 623/22.36; 623/22.24

(58) Field of Classification Search
USPC ........................... 623/22.35–22.37
See application file for complete search history.

(56) References Cited

U.S. PATENT DOCUMENTS

| | | |
|---|---|---|
| 3,641,590 A | 2/1972 | Michele |
| 3,685,058 A | 8/1972 | Tronzo |
| 4,062,891 A | 12/1977 | Remy |
| 4,563,778 A | 1/1986 | Roche et al. |
| 4,792,337 A | 12/1988 | Muller |
| 4,792,339 A | 12/1988 | Tepi |
| 4,795,469 A | 1/1989 | Oh |
| 4,813,961 A | 3/1989 | Sostegni |
| 4,822,367 A | 4/1989 | Stuhmer |
| 4,828,565 A | 5/1989 | Duthoit et al. |
| 4,840,632 A | 6/1989 | Kampner |
| 4,871,368 A | 10/1989 | Wagner |
| 4,955,825 A | 9/1990 | Groth et al. |
| 5,021,062 A | 6/1991 | Adrey et al. |
| 5,290,281 A | 3/1994 | Tschakaloff |
| 5,310,408 A | 5/1994 | Schryver et al. |
| 5,360,452 A | 11/1994 | Engelhardt et al. |
| 5,534,032 A * | 7/1996 | Hodorek ................ 623/20.32 |
| 5,590,281 A | 12/1996 | Stevens |
| 5,601,553 A | 2/1997 | Trebing et al. |
| 5,607,427 A | 3/1997 | Tschakaloff |
| 5,709,686 A | 1/1998 | Talos et al. |
| 5,888,204 A | 3/1999 | Ralph et al. |
| 5,954,722 A | 9/1999 | Bono |
| 5,961,524 A | 10/1999 | Crombie |
| 6,004,323 A | 12/1999 | Park et al. |
| 6,206,881 B1 | 3/2001 | Frigg et al. |
| 6,322,562 B1 | 11/2001 | Wolter |
| 6,605,090 B1 | 8/2003 | Trieu et al. |

(Continued)

*Primary Examiner* — Bruce E Snow
*Assistant Examiner* — Brian Dukert
(74) *Attorney, Agent, or Firm* — Harness, Dickey

(57) ABSTRACT

An acetabular cup system includes an acetabular cup having a wall with an inner surface and an outer surface. The acetabular cup includes a fixation opening through the wall, the fixation opening including a first wall portion adjacent to the inner surface and a second wall portion adjacent to the outer surface. The acetabular cup system also includes a fixation fastener including a head and a shaft with a bone-anchoring portion. The fastener can be inserted though the fixation opening. The head includes a first head portion engageable with the first wall portion and a second head portion engageable with the second wall portion.

16 Claims, 9 Drawing Sheets

(56) References Cited

U.S. PATENT DOCUMENTS

| | | |
|---|---|---|
| 6,679,883 B2 | 1/2004 | Hawkes et al. |
| 6,695,845 B2 | 2/2004 | Dixon et al. |
| 7,172,593 B2 | 2/2007 | Trieu et al. |
| 7,195,633 B2 | 3/2007 | Medoff et al. |
| 7,635,447 B2 | 12/2009 | Hamman et al. |
| 2004/0260291 A1 | 12/2004 | Jensen |
| 2006/0116678 A1 | 6/2006 | Impellizzeri |
| 2006/0235400 A1 | 10/2006 | Schneider |
| 2006/0241781 A1 | 10/2006 | Brown et al. |
| 2007/0055249 A1 | 3/2007 | Jensen et al. |
| 2007/0162147 A1 | 7/2007 | Lewis et al. |
| 2009/0210067 A1 | 8/2009 | Meridew |

\* cited by examiner

ACETABULAR CUP FIXATION

CROSS-REFERENCE TO RELATED APPLICATIONS

This application is a division of U.S. patent application Ser. No. 12/370,951, filed on Feb. 13, 2009, which claims the benefit of U.S. Provisional Application No. 61/030,027, filed on Feb. 20, 2008. The entire disclosures of the above applications are incorporated herein by reference.

INTRODUCTION

Acetabular cups are used with various fixation fasteners that can secure the cups to the bone in orthopedic procedures. The present teachings provide various methods and devices for securing acetabular cups to bone with locking fixation fasteners.

SUMMARY

The present teachings provide various acetabular cup systems and methods of locking fixation fasteners to acetabular cups and preventing loosening and back out of the fixation fasteners during use.

The present teachings provide an acetabular cup system that includes an acetabular cup having a wall with an inner surface and an outer surface. The acetabular cup includes a fixation opening through the wall, the fixation opening including a first wall portion adjacent to the inner surface and a second wall portion adjacent to the outer surface. The acetabular cup system also includes a fixation fastener including a head and a shaft with a bone-anchoring portion. The fastener can be inserted though the fixation opening. The head includes a first head portion engageable with the first wall portion and a second head portion engageable with the second wall portion.

In another aspect, the acetabular cup system includes an acetabular cup having a wall with an inner surface and an outer surface, the acetabular cup including a fixation opening through the wall, the fixation opening including a first wall portion adjacent to the inner surface and a second wall portion adjacent to the outer surface, the first wall portion being internally threaded and the second wall portion being unthreaded and tapered. The acetabular cup system also includes a fixation fastener including a head and a shaft with a bone anchoring portion, the fastener insertable though the fixation opening, the head including a first head portion threadably engageable with the first wall portion and a second head portion tapered for taper lock connection with the second wall portion.

In another aspect, the acetabular cup system includes an acetabular cup having a wall with an inner surface and an outer surface, the acetabular cup including a fixation opening through the wall, the fixation opening having an unthreaded surface, and a fixation fastener including a head and a shaft with a bone anchoring portion, the fastener insertable though the fixation opening, the head including a threaded portion with self-tapping threads threadably engageable with the fixation opening.

In a further aspect, the acetabular cup system includes an acetabular cup having a wall with an inner surface and an outer surface, the acetabular cup including a fixation opening through the wall, the fixation opening having a threaded portion, and a fixation fastener including an inner head attached to a bone-anchoring shaft and an outer head pivotably coupled to the inner head, the outer head including a threaded portion threadably engageable with the fixation opening, the inner head including a driver engagement recess.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

Figure 1:
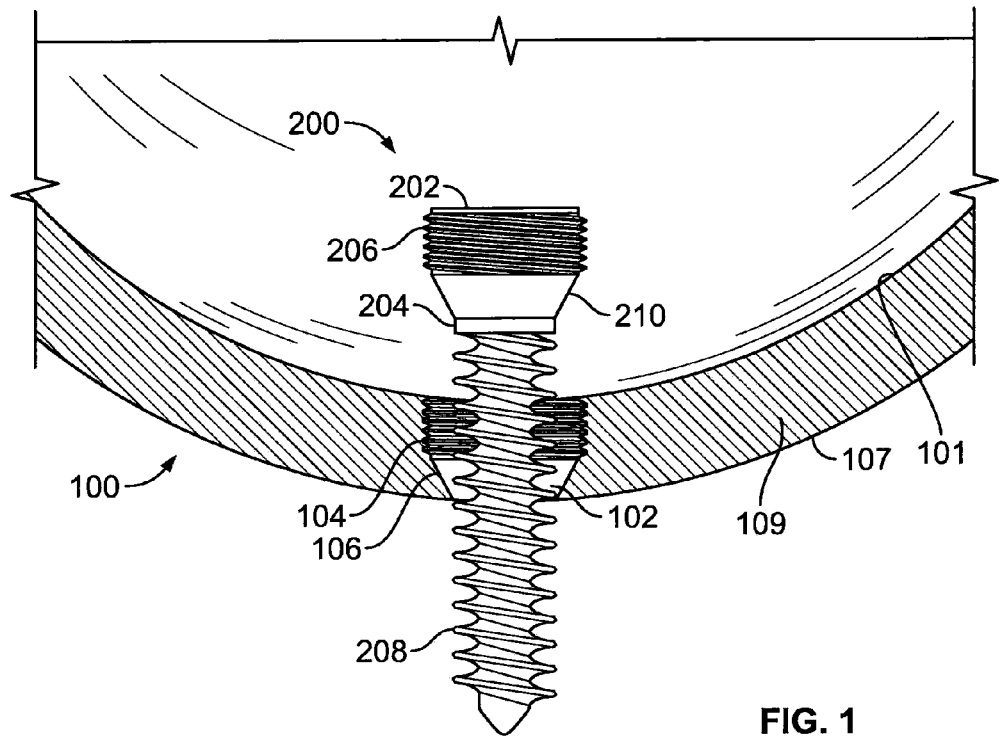
FIG. 1 is a sectional elevation view of an acetabular cup and a fixation fastener according to the present teachings.

The following description is merely exemplary in nature and is in no way intended to limit the present teachings, applications, or uses. For example, although the present teachings illustrate various fasteners for use with acetabular cups, the present teachings can be used for fixation of fasteners to other prosthetic components.

The present teachings provide various aspects related to the fixation of acetabular cups to bone through the use of fixation fasteners and preventing loosening or back out of the fasteners during use. Any type of acetabular cups can be used, including, but not limited to, porous metal acetabular cups, such as porous titanium cups, and the Regenerex™ cup, commercially available from Biomet, Inc., of Warsaw, Ind. Methods for fabricating acetabular cups and other implant components from porous metal material are described in co-pending and commonly assigned patent application Ser. No. 11/357929, filed Feb. 17, 2006, the disclosure of which is incorporated by reference herein.

Referring to FIGS. 1-10, an exemplary acetabular cup 100 can include a wall 109 having a concave inner surface 101 and a convex outer surface 107. The wall 109 can include one or more fixation holes or other through openings 102 for receiving corresponding fixation fasteners 200. An exemplary fixation fastener 200 can generally include a head 202 and a shaft or shank 204 with a threaded portion 208 for anchoring into the acetabular bone.

Figure 2:
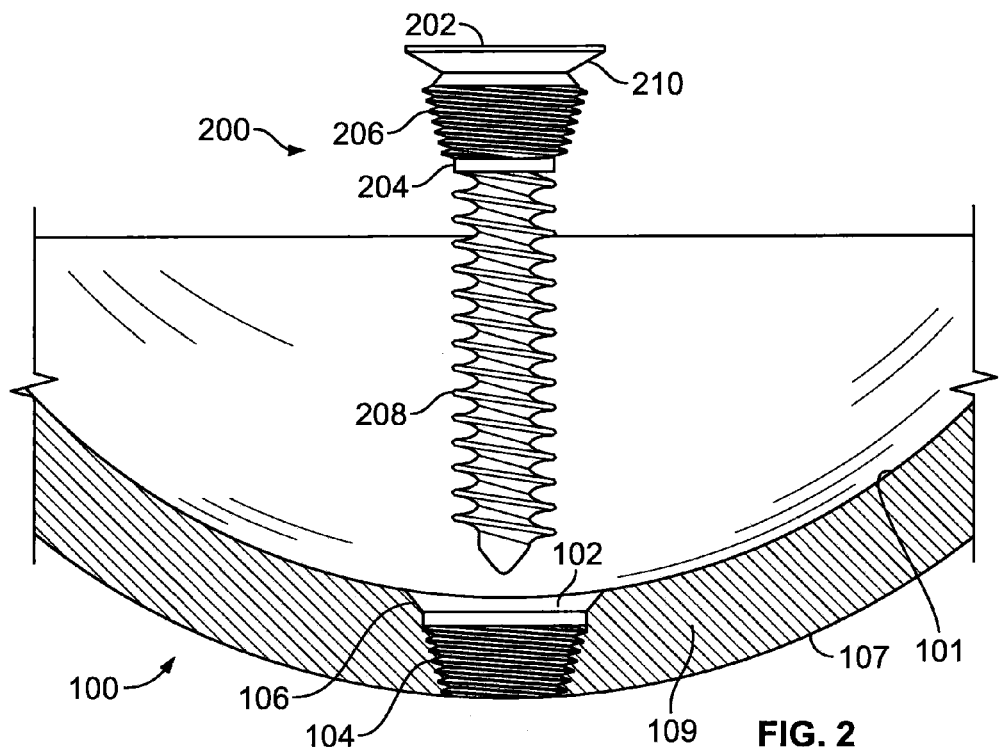
FIG. 2 is a sectional elevation view of an acetabular cup and a fixation fastener according to the present teachings.

Referring to FIGS. 1 and 2, the head 202 of the fastener 200 can include a male threaded portion 206 and a male tapered portion 210. The tapered portion 210 of the head 202 can taper toward the shank 204 of the fastener 200. The fixation opening 102 of the cup 100 can similarly have a female threaded portion 104 and a female tapered portion 106. The tapered portion 210 of the head 202 of the fastener 200 and the tapered portion 106 in the opening 102 of the acetabular cup 100 can have appropriate taper angles to form a taper lock connection. Accordingly, as the threaded portion 206 of the head 202 engages the threaded portion 104 of the opening 102 of the cup 100, the tapered portion 210 of the head 202 of the fastener 200 can mate and taper lock with the tapered portion 106 of the opening 102, locking the fastener 200 to the cup 100.

In the exemplary illustration of FIG. 1, the tapered portion of the head 202 is adjacent to the shank 204, and the tapered portion 106 of the cup 100 is adjacent the outer convex surface of the cup 100. In the exemplary illustration of FIG. 2, the positions of the tapered and threaded portions are reversed. Specifically, the threaded portion 206 of the head 202 is adjacent the shank 204 and the threaded portion 104 of the opening 102 is adjacent the outer convex surface of the cup 100. Referring to FIG. 2, the threaded portion 206 of the head 202 and the threaded portion 104 of the opening 102 can be tapered, as shown in FIG. 2, or straight, similarly to FIG. 1.

Figure 3:
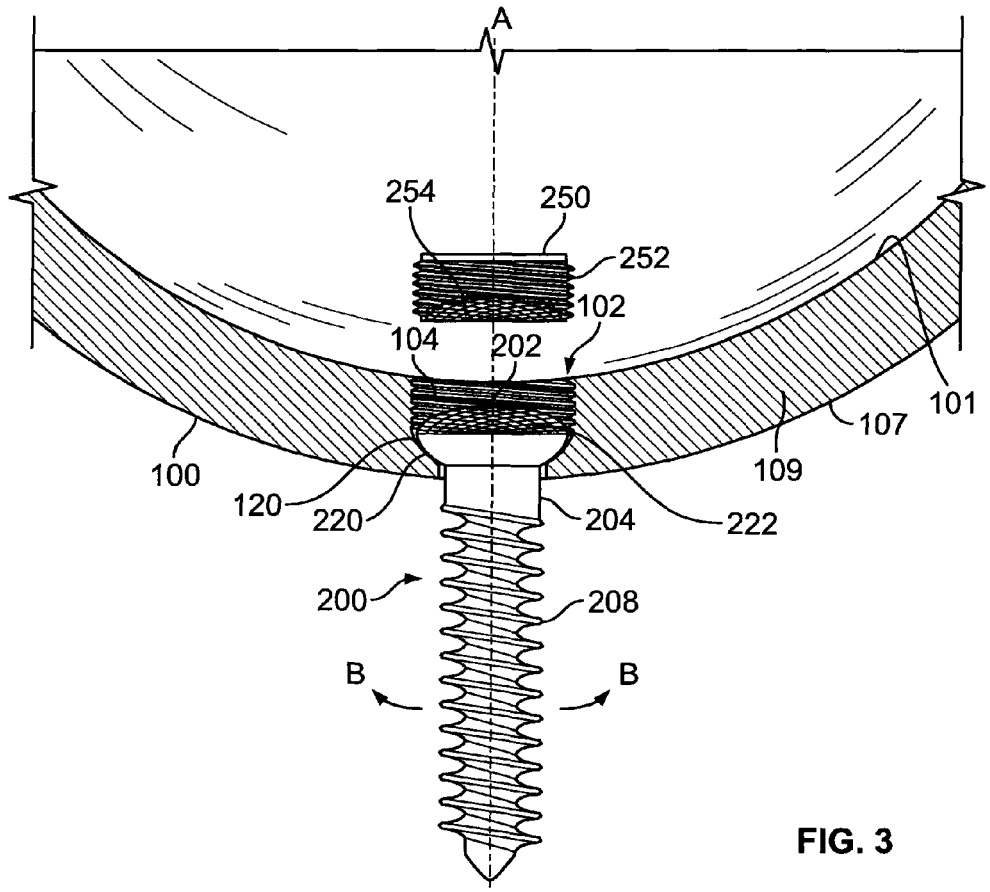
FIG. 3 is a sectional elevation view of an acetabular cup, a fixation fastener and a locking cap according to the present teachings.

Referring to FIG. 3, the head 202 of the fastener 200 can include a curved or rounded or spherical undersurface 220 and a rounded upper surface 222 that can be textured. In addition, the opening 102 in the acetabular cup 100 can have a similarly curved or rounded or spherical lower portion 120 configured to receive the undersurface 220 of the head 202 of fastener 200 adjustably, such that the fastener 200 can angulate or pivot in the direction of the curved arrows B relative to an axis A passing through the center of the opening 102. The opening 102 of the acetabular cup 100 can include a threaded portion 104 above the spherical portion 120. The threaded portion 104 of the opening 102 can engage the external threads 252 of a threaded washer or other locking cap or locking member 250. The threaded washer 250 can include a textured undersurface 254 that can engage the textured upper surface 222 of the head 202 of the fastener 200. In operation, the fastener 200 can be positioned within the opening 102 of the acetabular cup 100, adjustably angled relative to the axis A of the opening 102 and threaded into the bone. Once the fastener 200 is anchored into the bone, the threaded washer 250 can be inserted into the opening 102 and rotated such that the undersurface 254 of the threaded washer 250 engages the upper surface 222 of the head 202 of the fastener 200, thereby locking the fastener 200 in the acetabular cup 100 and the bone and preventing back out of the fastener 200 during use.

Figure 4:
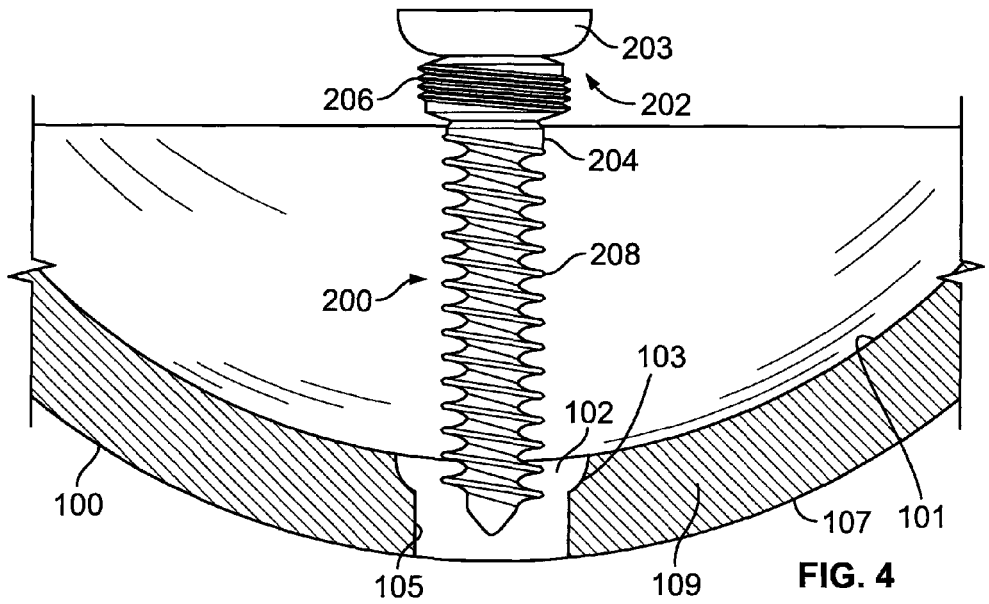
FIG. 4 is a sectional elevation view of an acetabular cup and a fixation fastener according to the present teachings.

Referring to FIG. 4, the head 202 of the fastener 200 can include a curved or spherical portion 203 and a threaded portion 206, which can be cylindrical. The threads of the threaded portion 206 can be self tapping. The opening 102 in the acetabular cup 100 can include a corresponding spherical portion 103 that can engage the spherical portion 203 of the head 202 of the fastener 200. The opening 102 in the acetabular cup 100 can also include a cylindrical portion 105. During insertion, the self-tapping threaded portion 206 on the head 202 of the fastener 200 can tap threads into the wall of the cylindrical portion 105 of the opening 102, until the head 202 of the fastener 200 is fully seated in the opening 102 and secured to the cup 100. In this respect, the acetabular cup 100 can be made of porous metal, such as porous titanium, Regenerex™, or other biocompatible material that can be relatively easily tapped.

Figure 5:
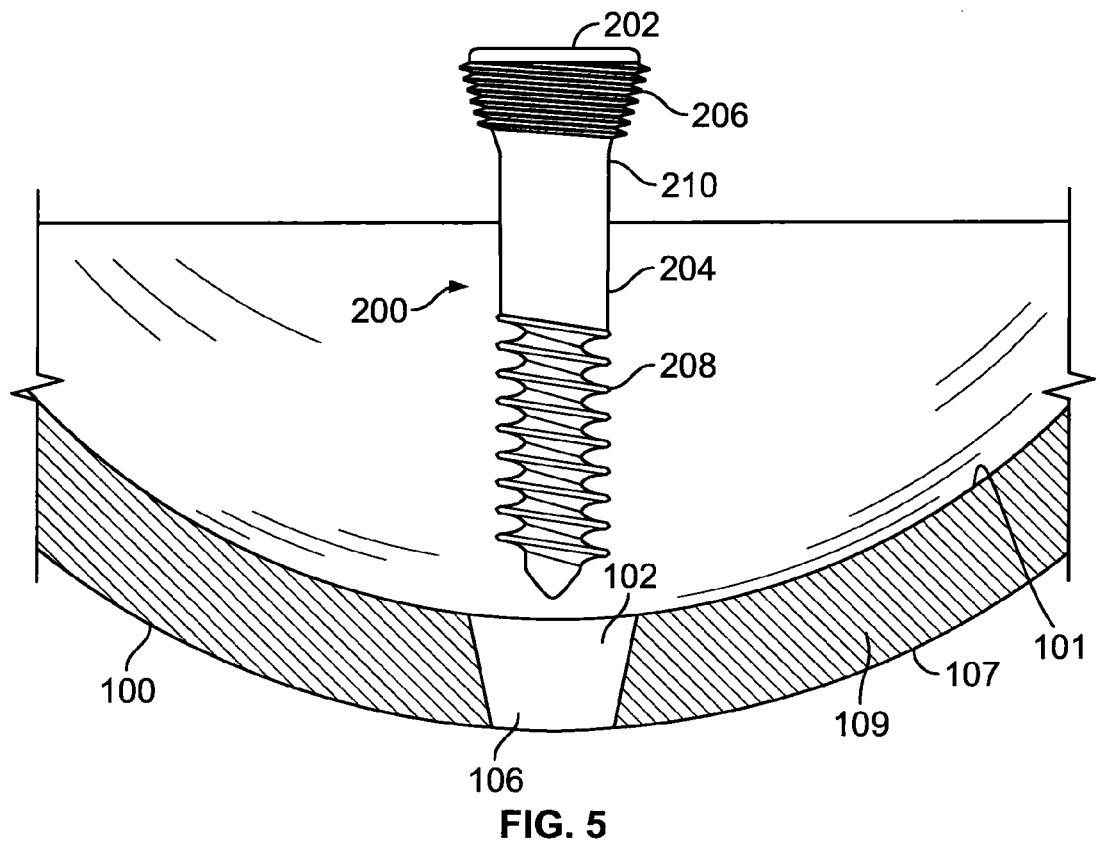
FIG. 5 is a sectional elevation view of an acetabular cup and a fixation fastener according to the present teachings.

Referring to FIG. 5, the head 202 of the fastener 200 can include a tapered threaded portion 206 with self-tapping threads which can cut into the similarly tapered opening 102 of the acetabular cup 100. The acetabular cup 100 can be made of porous metal for tapping by the self-tapping threaded portion 206 of the head 202 of the fastener 200, as discussed above in connection with FIG. 4.

Figure 6:
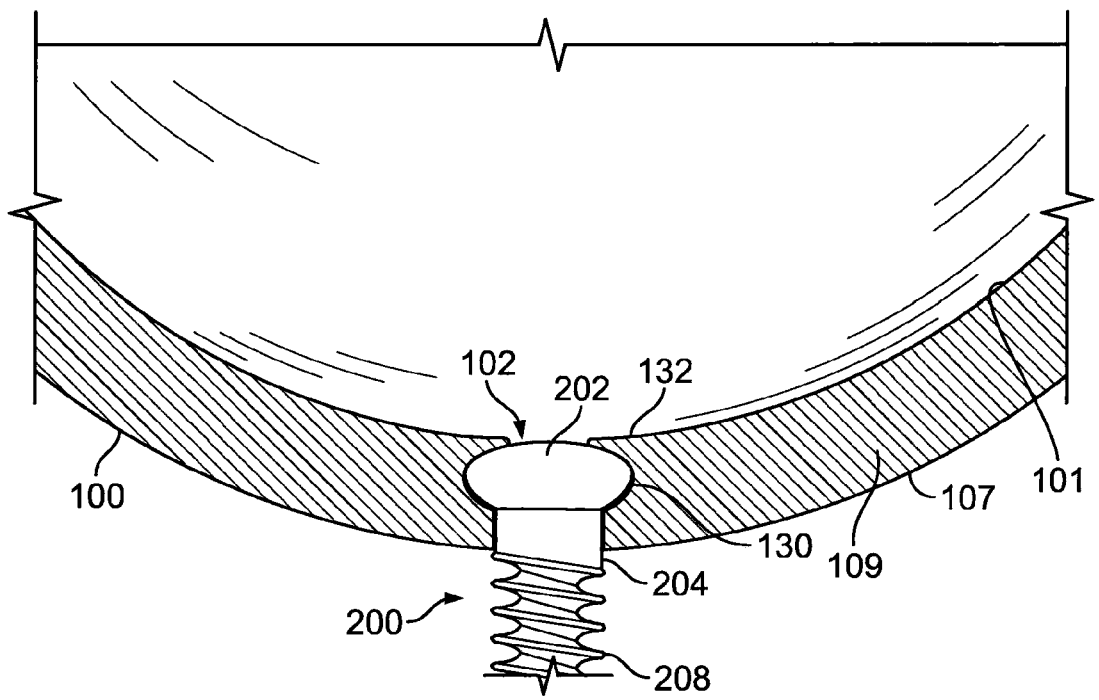
FIG. 6 is a sectional elevation view of an acetabular cup and a fixation fastener according to the present teachings.

Referring to FIG. 6, the acetabular cup 100 can be made of porous metal that can be peened or otherwise plastically deformed. The head 202 of the fastener 200 is inserted through the opening 102 and positioned on a pocket or seat 130 defined by the opening 102. An area 132 of the acetabular cup 100 immediately surrounding the upper portion of the opening 102 adjacent to the head 202 of the fastener 200 can be peened or otherwise deformed with a tool such that the deformed area 132 can overlap a portion of the head 202 and trap the head 202 in the seat 130 preventing the fastener 200 from backing out of the opening 102 during use.

Figure 7:
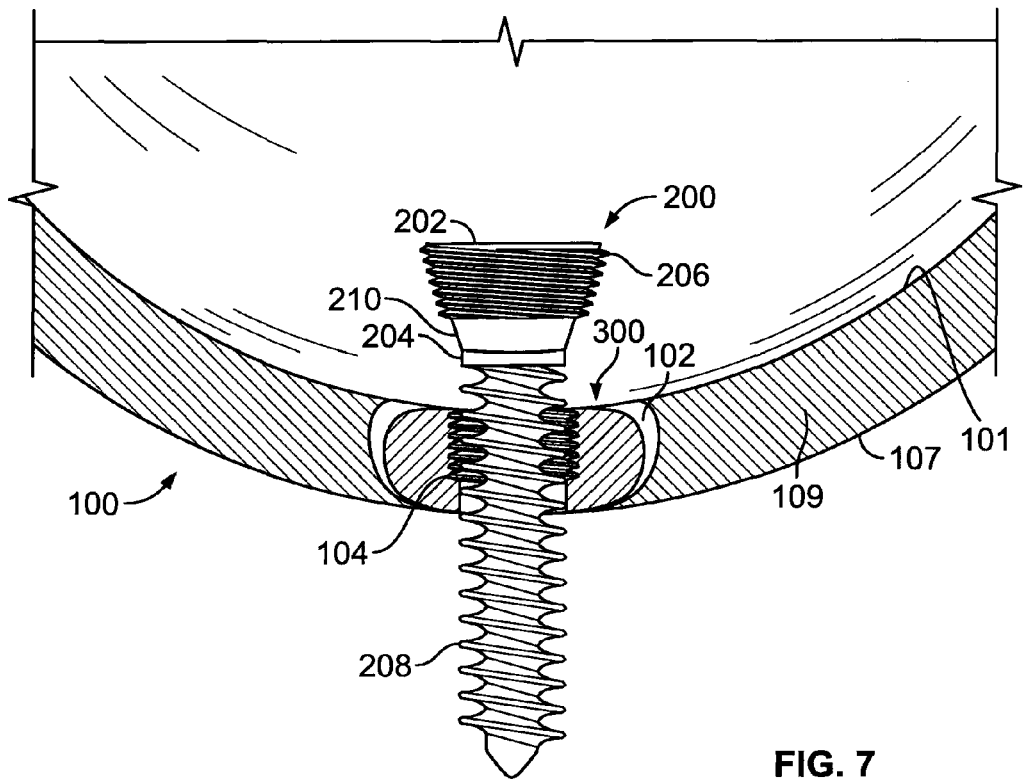
FIG. 7 is a sectional elevation view of an acetabular cup, a fixation fastener and an insert according to the present teachings.
Figure 7A:
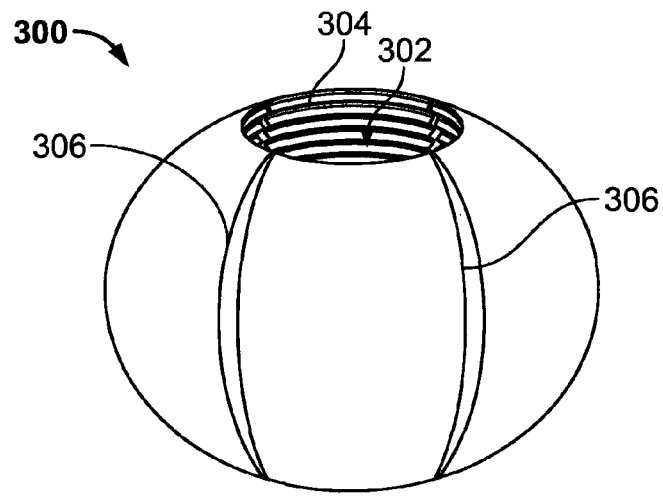
FIG. 7A is a perspective view of the insert of FIG. 7.

Referring to FIGS. 7 and 7A, the opening 102 of the cup 100 can be spherically shaped and rotatably receive a spherically shaped insert 300. The insert 300 can include a through bore 302 having internal threads 304. The insert 300 can include meridian slits 306 that allow expansion of the insert 300. The head 202 of the fastener 200 can include a tapered portion 210, which can be fully or partially threaded with threads 206. The fastener 200 can be inserted through the bore 302, and the head 202 of the fastener 200 can be threadably engaged with the threads 304 of the insert 300, forcing the insert 300 to expand. The expansion of the insert 300 lockingly engages the insert 300 to the opening 102 of the acetabular cup 100 and prevents rotational movement between the insert 300 and the acetabular cup 100. Before the fastener 200 is inserted, the insert 300 can move in a limited manner with respect to the acetabular cup 100 so as to permit optimal positioning of the fastener 200 with respect to the cup 100 before securing the fastener 200 to the cup 100.

Figure 8:
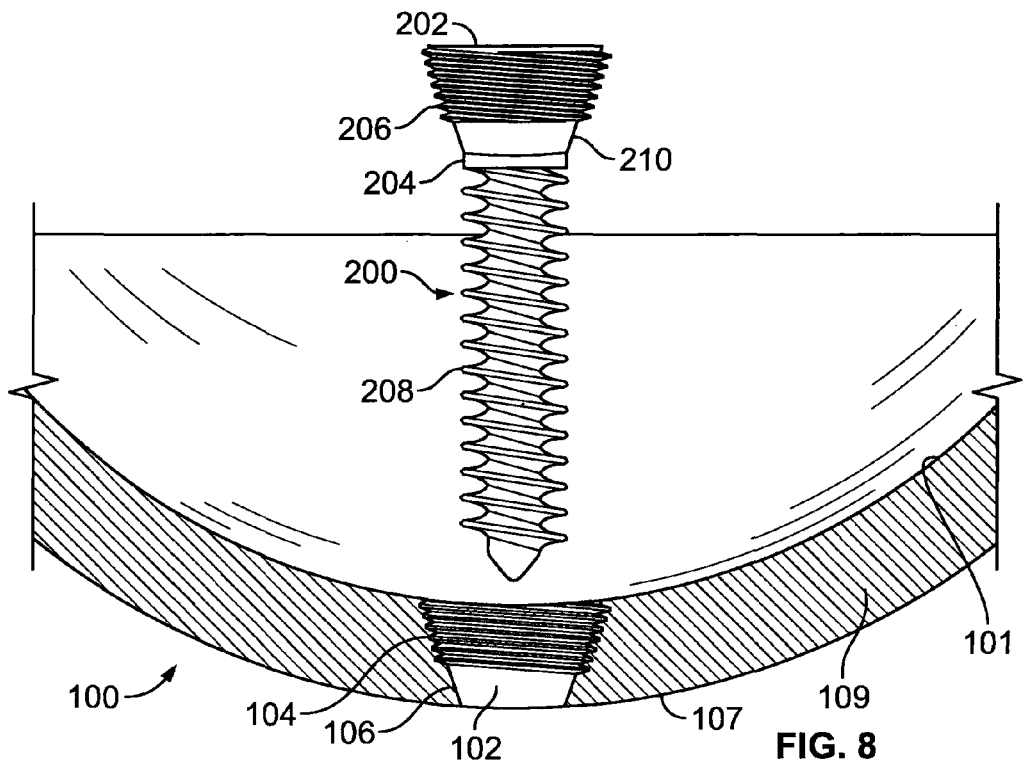
FIG. 8 is a sectional elevation view of an acetabular cup and a fixation fastener according to the present teachings.

Referring to FIG. 8, the opening 102 in the acetabular cup 100 can include a fully threaded portion 104 engaging a corresponding threaded portion 206 of the head 202 of the fastener 200. The opening 102 and the head 202 can be straight or tapered and can be fully threaded or have respective unthreaded portions 106 and 210.

Figure 9:
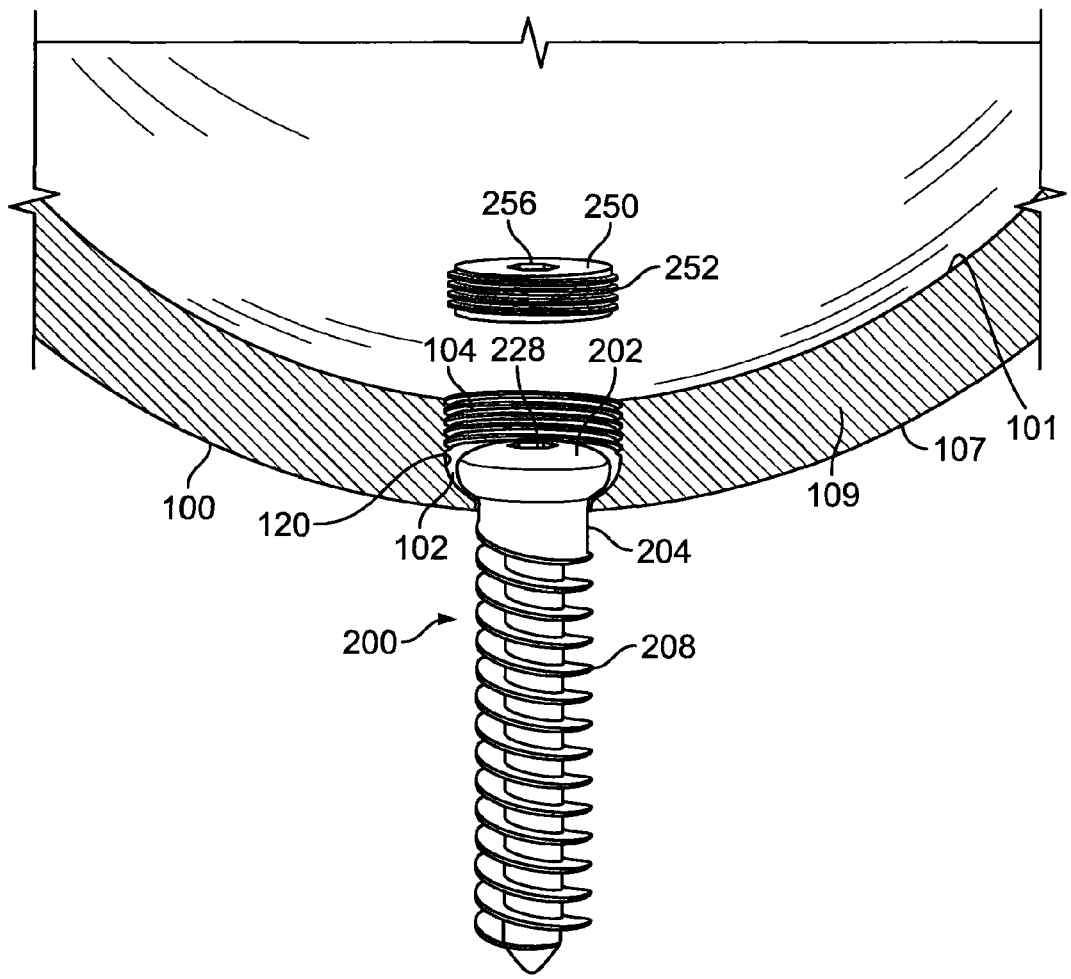
FIG. 9 is a sectional elevation view of an acetabular cup, a fixation fastener and a locking cap according to the present teachings.

Referring to FIG. 9, the fixation fastener 200 can include a spherical head 202 with a hex or otherwise shaped recess 228 in its upper surface to allow the fastener 200 to be rotated by an appropriate driver. The opening 102 of the acetabular cup 100 can include an upper internally threaded portion 104 and a lower spherical portion defining a seat 120. The fastener 200 can be inserted into the opening 102 of the acetabular cup 100 such that the head 202 of the fastener 200 is received in the seat 120 of the acetabular cup 100. A locking nut 250 having external threads 252 and a recess 256 for a driver can be threadably engaged with the threaded portion 104 of the opening 102, thereby locking the head 202 of the fastener 200 to the acetabular cup 100.

Figure 10:
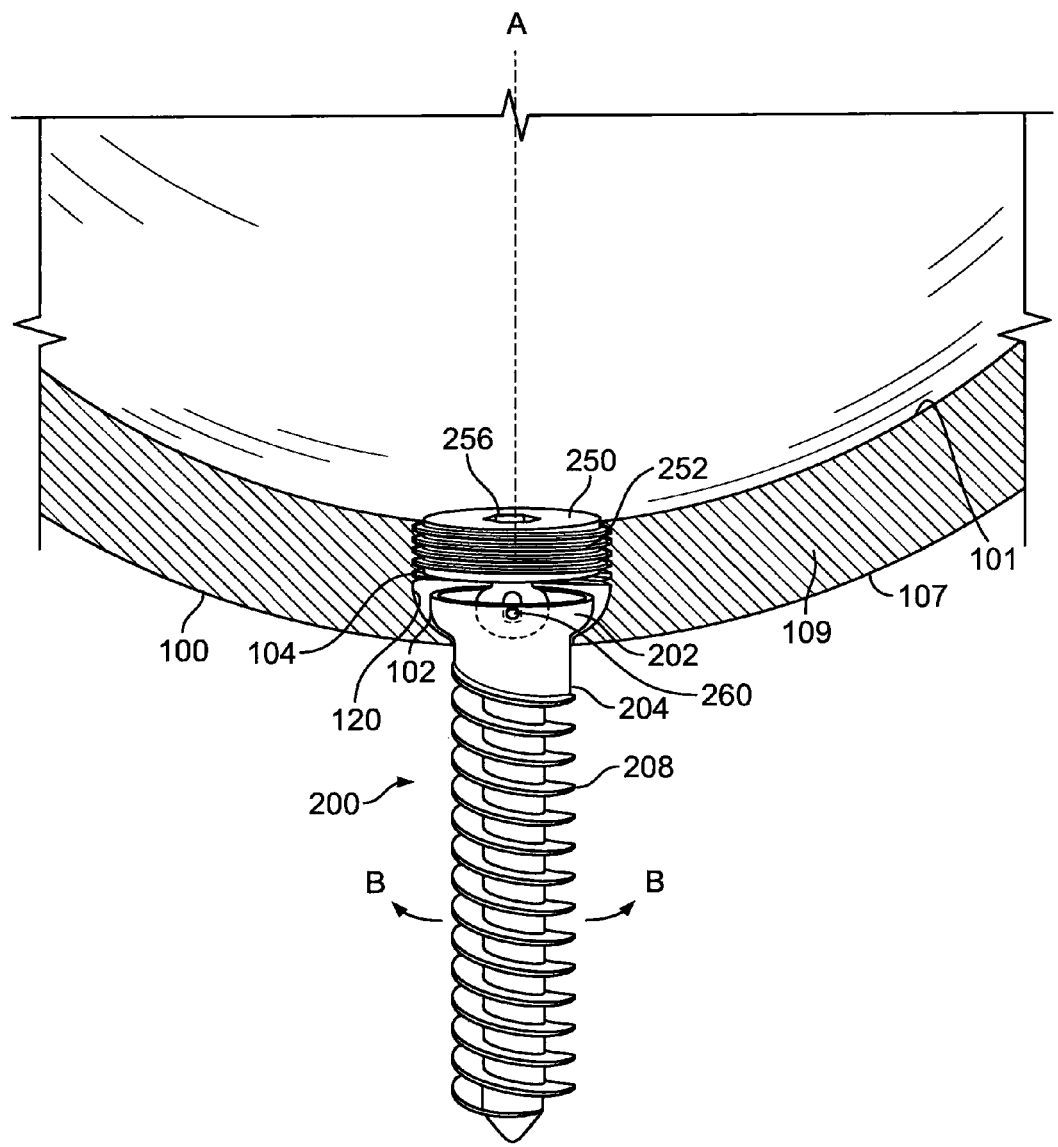
FIG. 10 is a sectional elevation view of an acetabular cup, and a two-piece fixation fastener according to the present teachings.

Referring to FIG. 10, the opening 102 of the acetabular cup 100 is similar to the opening 102 shown in FIG. 9. The fastener 200 can include a head 202 in the form of a spherical cavity. A locking washer 250 can be pivotably coupled to the head 202 of the fastener 202 with a pivot pin 260 forming a two-piece fixation construct. The pivot pin 260 allows the shank 204 of the fastener 200 to angulate relative to the washer 250 such that the shank 204 can be inserted at various angles relative to the axis A of the opening 102, while maintaining the ability to prevent back out by threadably engaging the locking washer 250 to the internal threaded portion 104 of the opening 102 of the acetabular cup 100.

Figure 11:
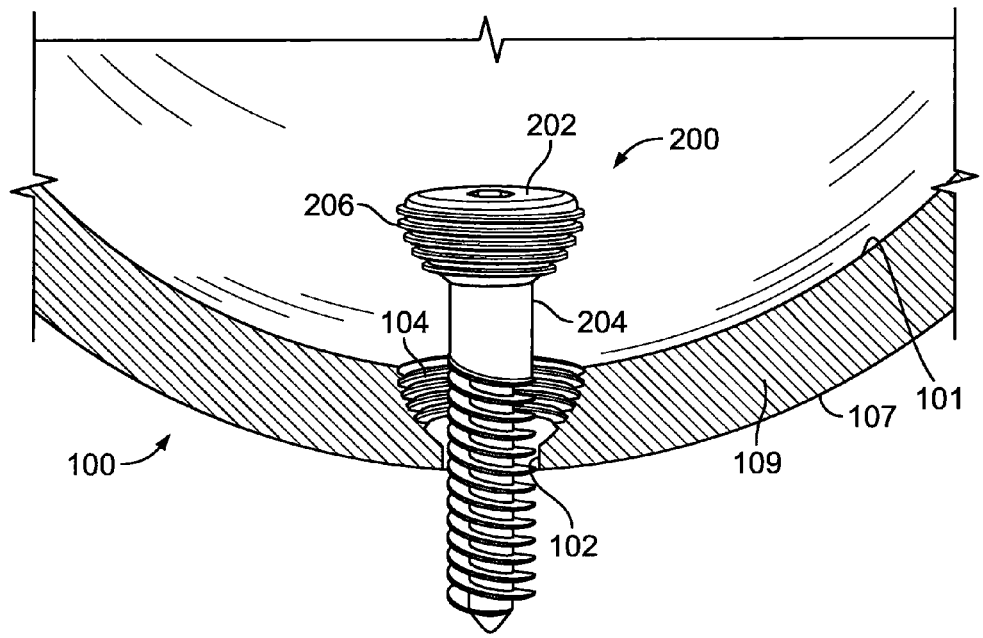
FIG. 11 is a sectional elevation view of an acetabular cup and a fixation fastener according to the present teachings.

Referring to FIG. 11, the fixation fastener 200 can include at least a spherical head portion or, alternatively, a spherical head 202 having an external threaded portion 206. The threaded head 202 of the fastener can be received in a threaded spherical socket 104 defined in the opening 102 of the acetabular cup 100. Further, the threaded head 202 of the fastener can be rotated and inserted at an angle not aligned with the axis of the opening 102, such that the threads of the head 202 of the fastener 200 and the threads of the opening 102 of the acetabular cup 100 can cross-thread and lock.

Figure 12:
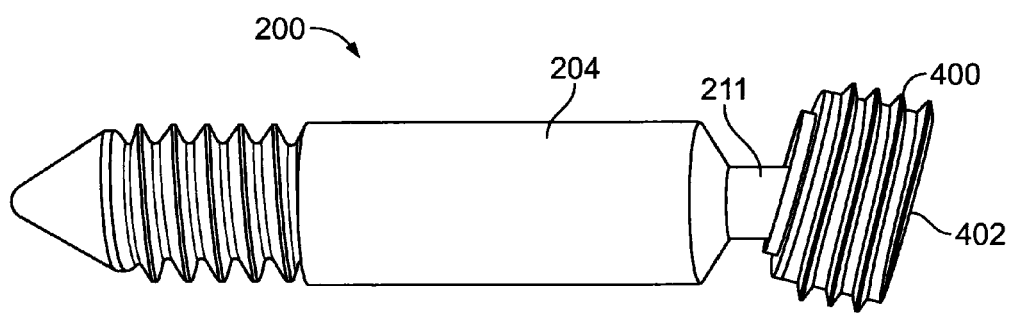
FIG. 12 is a perspective view of a variable angle locking fixation fastener according to the present teachings.
Figure 12A:
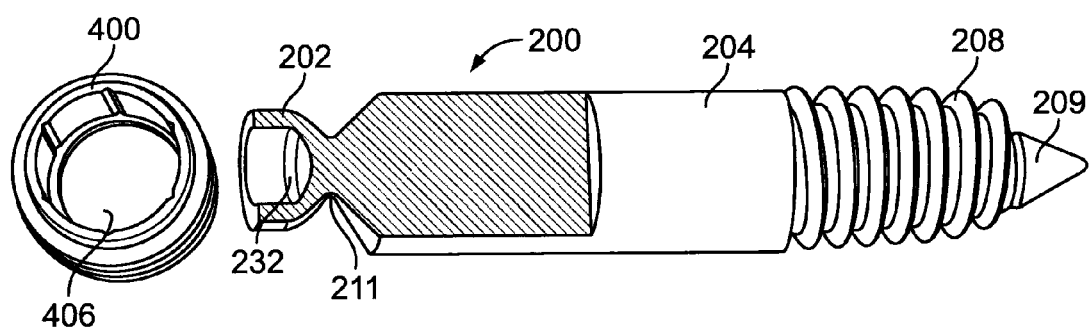
FIG. 12A is an exploded and partially sectional view of the fixation fastener of FIG. 12.
Figure 12B:
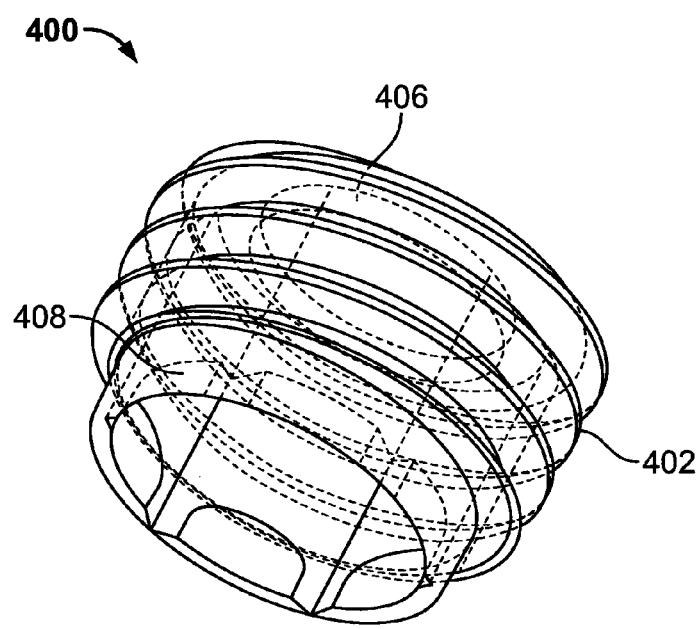
FIG. 12B is a perspective view of the outer head of the fixation fastener of FIG. 12.
Figure 12C:
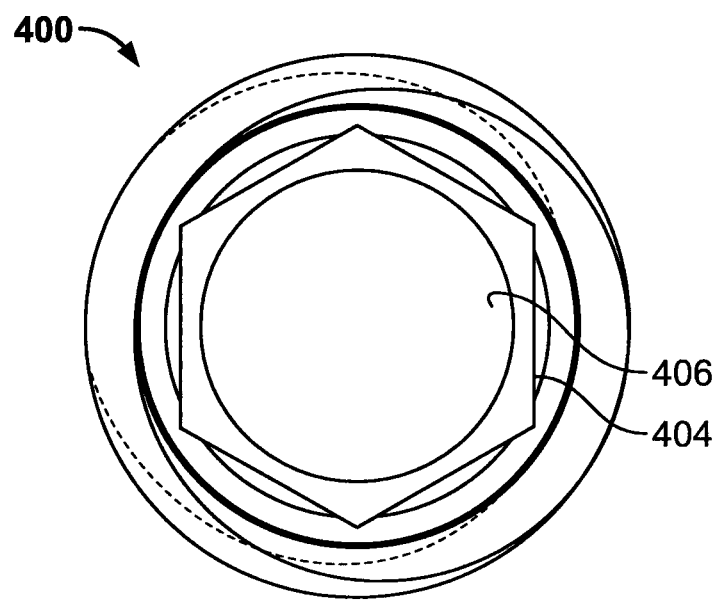
FIG. 12C is a plan view of the outer head of FIG. 12B.
Figure 12D:
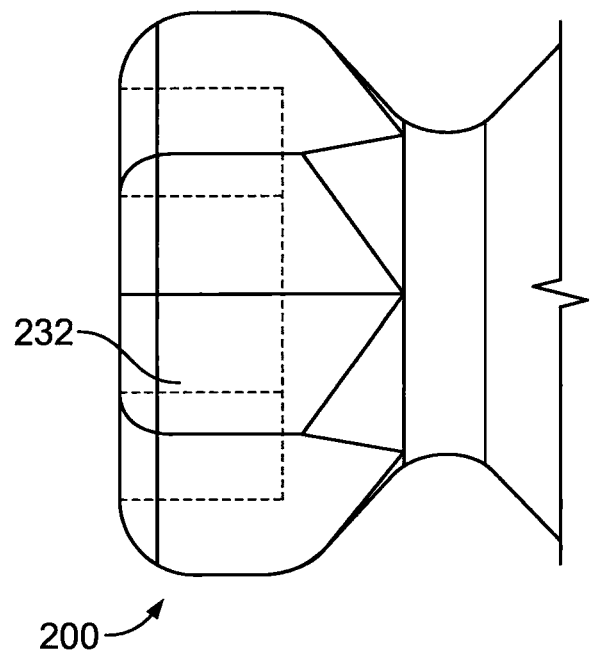
FIG. 12D is a side view detail of the fixation fastener of FIG. 12, showing the inner head of the fixation fastener.

Referring to FIGS. 12-12D, various aspects of a variable angle locking fastener 200 are illustrated. The fastener 200 can include an inner head 202 fixedly connected to a shank 204 with a neck portion 211, and an outer head 400 pivotably coupled with the inner head 202. The inner head 202 can include a driver engaging recess 232. The shank 204 can include a threaded portion 208 and an anchoring distal tip 209. The inner head 202 can be pivotably received in an opening 406 of the outer head 400. The outer head 400 can include outer threads 402 for threadably locking the fixation fastener 200 into a threaded opening of an acetabular cup or other implant. The outer head 400 can include a driver engagement feature 404 and an end lip 408 that can be swaged or otherwise deformed to capture the inner head 202. The threaded outer head 400 can lock the fixation fastener 200 into a similarly threaded hole of an acetabular cup 100, or a fixation plate or other implant, preventing back out of the fixation fastener 200, while allowing angulation of the shank 204 for anchoring the fixation fastener 200 at a selected orientation.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings that various changes, modifications and variations can be made therein without departing from the spirit and scope of the present teachings.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An acetabular cup system comprising:
an acetabular cup having a wall with an inner surface and an outer surface, the acetabular cup including a fixation opening through the wall, the fixation opening including a first wall portion adjacent to the inner surface and a second wall portion adjacent to the outer surface; and
a fixation fastener including a head and a shaft with a bone-anchoring portion, the fixation fastener insertable though the fixation opening, the head including a first head portion engageable with the first wall portion and a second head portion engageable with the second wall portion, wherein the first head portion is substantially spherical and has an unthreaded surface that extends towards a central axis of the fixation fastener past a thread of the second head portion and the second head portion is cylindrical and the thread is a self-tapping thread configured to cut into the second wall portion.

2. The acetabular cup system of claim 1, wherein the fixation opening is unthreaded and the first wall portion is substantially spherical and the second wall portion is substantially cylindrical.

3. The acetabular cup system of claim 1, wherein the acetabular cup comprises porous metal.

4. The acetabular cup system of claim 1, wherein the acetabular cup comprises a biocompatible material that can be tapped by the thread of the head of the fastener.

5. An acetabular cup system comprising:
an acetabular cup having a wall with an inner surface and an outer surface, the acetabular cup including a fixation opening through the wall, the fixation opening having an unthreaded surface with a spherical portion extending from the inner surface and a cylindrical portion having a single constant diameter extending an entire distance from the spherical portion to the outer surface; and a fastener including a head with a first threaded portion and a shaft with a bone anchoring portion and a second threaded portion, wherein the fastener is insertable through the fixation opening, wherein the first threaded portion includes cutting threads to threadably engage an entire circumference of a cylindrical portion of the fixation opening, and wherein the second threaded portion includes threads different from the cutting threads to threadably engage a bone portion.

6. The acetabular cup system of claim 5, wherein the head of the fixation fastener includes a spherical portion mateable with the spherical portion of the fixation opening.

7. The acetabular cup system of claim 5, wherein the acetabular cup comprises porous metal.

8. The acetabular cup system of claim 1, wherein the acetabular cup comprises a biocompatible material that can be tapped by the threads of the head of the fastener.

9. An acetabular cup system comprising:

an acetabular cup having a wall with an inner surface and an outer surface, the acetabular cup including a fixation opening through the wall, the fixation opening having an unthreaded surface with a spherical portion extending directly from the inner surface and a cylindrical portion having a single constant diameter extending directly from the spherical portion an entire distance to the outer surface; and a fastener including a head and a shaft with a bone anchoring portion, the fastener insertable though the fixation opening, the head including an unthreaded spherical portion mateable with the spherical portion of the fixation opening and a threaded portion extending directly from the spherical portion of the head and having self-tapping threads that cut threads into the cylindrical portion of the fixation opening and engages an entire circumference of the cylindrical portion of the fixation opening when the fixation fastener is fully seated in the fixation opening.

10. The acetabular cup system of claim 9, wherein the acetabular cup comprises porous metal.

11. The acetabular cup system of claim 2, wherein the self-tapping threads engage substantially an entire circumference of the second wall portion of the fixation opening.

12. The acetabular cup system of claim 1, wherein the self-tapping thread is configured to cut into the second wall portion as the first head portion is engaged into the first wall portion.

13. The acetabular cup system of claim 1, wherein the self-tapping thread has a greater outer circumference than a shaft thread that extends at least a portion of a length of the shaft.

14. The acetabular cup system of claim 5, wherein the cylindrical portion has substantially parallel walls that extend an entire distance from the spherical portion to the outer surface.

15. The acetabular cup system of claim 14, wherein the cutting threads are configured to tap threads into the substantially parallel walls of the cylindrical portion until the head of the fastener is fully seated in the fixation opening.

16. The acetabular cup system of claim 9, wherein the cylindrical portion has substantially parallel walls that extend the entire distance from the spherical portion to the outer surface.

* * * * *

UNITED STATES PATENT AND TRADEMARK OFFICE
CERTIFICATE OF CORRECTION

PATENT NO. : 8,556,985 B2  
APPLICATION NO. : 13/299663  
DATED : October 15, 2013  
INVENTOR(S) : Jason D. Meridew Page 1 of 1

It is certified that error appears in the above-identified patent and that said Letters Patent is hereby corrected as shown below:

Title Page:

Item (57) Column 2, Line 8, Abstract; delete "though" and insert --through--.

In the Specification:

Column 1, Line 34; delete "though" and insert --through--.

Column 1, Line 47; delete "though" and insert --through--.

Column 1, Line 57; delete "though" and insert --through--.

In the Claims:

Column 6, Line 44, Claim 1; delete "though" and insert --through--.

Column 7, Line 30, Claim 9; delete "though" and insert --through--.

Signed and Sealed this  
Twenty-ninth Day of April, 2014

Michelle K. Lee  
*Deputy Director of the United States Patent and Trademark Office*